US012611512B2

(12) United States Patent
Spataro et al.

(10) Patent No.: US 12,611,512 B2
(45) Date of Patent: Apr. 28, 2026

(54) CATHETER PLACEMENT DEVICE AND RELATED METHODS

(71) Applicant: Becton, Dickinson and Company, Franklin Lakes, NJ (US)

(72) Inventors: Joseph Spataro, Cottonwood Heights, UT (US); Yiping Ma, Layton, UT (US); Huy Tran, Riverton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 49 days.

(21) Appl. No.: 17/330,201

(22) Filed: May 25, 2021

(65) Prior Publication Data

US 2021/0386939 A1     Dec. 16, 2021

Related U.S. Application Data

(60) Provisional application No. 63/038,587, filed on Jun. 12, 2020.

(51) Int. Cl.
*A61M 5/42*         (2006.01)
*A61B 17/135*       (2006.01)
*A61M 25/02*        (2006.01)

(52) U.S. Cl.
CPC ......... *A61M 5/427* (2013.01); *A61B 17/1355* (2013.01); *A61M 25/02* (2013.01); (Continued)

(58) Field of Classification Search
CPC ...... A61M 5/427; A61M 5/158; A61M 25/02; A61M 2025/0206; A61M 2025/0213;

A61M 2205/0272; A61M 2205/3313; A61M 2205/3584; A61M 2205/52; A61M 2205/583; A61M 2205/052; A61M 2205/50; A61M 2205/581; A61M 2205/8206; A61M 2207/00; A61B 17/1355; A61B 17/1322; A61B 17/135; (Continued)

(56) References Cited

U.S. PATENT DOCUMENTS 5,190,530 A * 3/1993 Greeff .................. A61M 25/02
                                               604/179
6,074,364 A     6/2000 Paul
(Continued)

FOREIGN PATENT DOCUMENTS

CN      1177304 A      3/1998
CN      107441613      12/2017
(Continued)

*Primary Examiner* — Laura A Bouchelle
*Assistant Examiner* — Sarah Dympna Grasmeder
(74) *Attorney, Agent, or Firm* — Kirton McConkie; Whitney Blair; Kevin Stinger

(57)        ABSTRACT

An intravenous (IV) therapy system to facilitate the insertion of a catheter or another suitable IV device into a patient may include a band made of flexible material to be secured around a limb of a patient. The IV therapy system may include a window formed through the band to provide access to the patient's body. The IV therapy system may include a tourniquet formed within the band to selectively apply a pressure against the patient's body. The IV therapy system may include a blood vessel indicator to indicate where the catheter or other suitable IV device is to be inserted.

18 Claims, 5 Drawing Sheets

(52) U.S. Cl.
CPC .............. *A61M 2025/0206* (2013.01); *A61M 2205/0272* (2013.01); *A61M 2205/3313* (2013.01); *A61M 2207/00* (2013.01)

(58) Field of Classification Search
CPC  A61B 2017/00154; A61B 2017/00199; A61B 2017/00876; A61B 5/489; A61F 13/10
See application file for complete search history.

(56)  References Cited

U.S. PATENT DOCUMENTS

| | | | | |
|---|---|---|---|---|
| 6,290,662 | B1 * | 9/2001 | Morris | A61H 9/0078 601/149 |
| 10,173,035 | B2 * | 1/2019 | Albany | A61M 25/02 |
| 10,517,606 | B1 * | 12/2019 | Donaldson | A61M 5/158 |
| 2009/0024062 | A1 * | 1/2009 | Einarsson | A61F 5/01 600/595 |
| 2011/0301500 | A1 * | 12/2011 | Maguire | A61B 34/76 600/583 |

| | | | | |
|---|---|---|---|---|
| 2013/0253447 | A1 | 9/2013 | Ball et al. | |
| 2014/0228818 | A1 * | 8/2014 | Brinton | A61M 25/02 604/544 |
| 2014/0249458 | A1 * | 9/2014 | Malhi | A61H 1/008 601/150 |
| 2017/0035335 | A1 | 2/2017 | Breteau et al. | |
| 2017/0361032 | A1 | 12/2017 | Kim | |
| 2018/0169389 | A1 | 6/2018 | Lemon et al. | |
| 2020/0375608 | A1 * | 12/2020 | Rittenhouse | A61B 17/135 |
| 2021/0212658 | A1 * | 7/2021 | McGrath | A61B 34/25 |

FOREIGN PATENT DOCUMENTS

| | | | | |
|---|---|---|---|---|
| CN | 215914775 | U | 3/2022 | |
| JP | H751276 | A | 2/1995 | |
| JP | 2010524521 | A | 8/2013 | |
| JP | 2016096919 | A | 5/2016 | |
| KR | 20200063643 | A | 6/2020 | |
| WO | 9855072 | A2 | 12/1998 | |
| WO | WO-2011038045 | A2 * | 3/2011 | A61M 39/10 |
| WO | 2019/232454 | | 12/2019 | |

* cited by examiner

500 ⬎

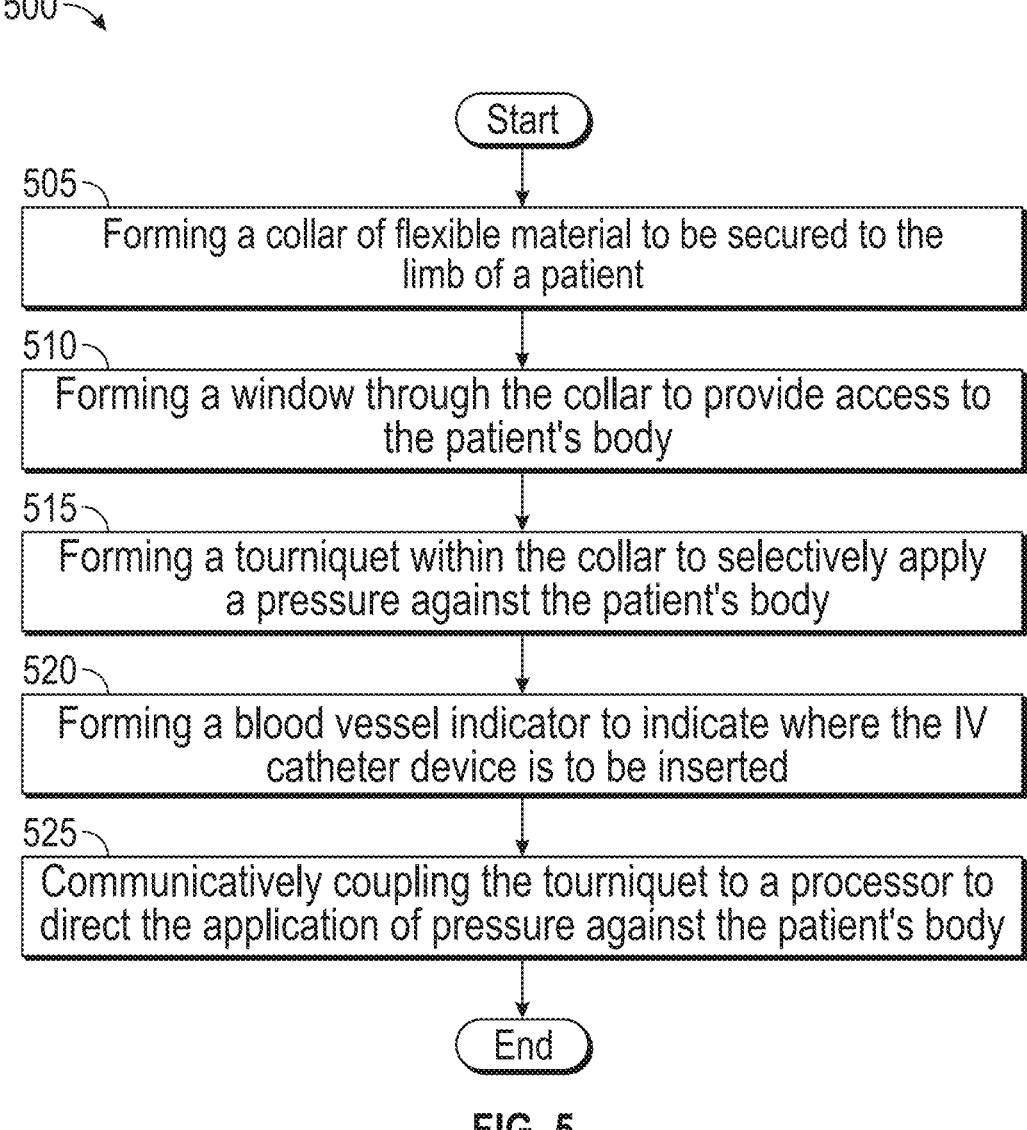

Start

505 ⬐
Forming a collar of flexible material to be secured to the limb of a patient 510 ⬐
Forming a window through the collar to provide access to the patient's body 515 ⬐
Forming a tourniquet within the collar to selectively apply a pressure against the patient's body 520 ⬐
Forming a blood vessel indicator to indicate where the IV catheter device is to be inserted 525 ⬐
Communicatively coupling the tourniquet to a processor to direct the application of pressure against the patient's body End

FIG. 5

CATHETER PLACEMENT DEVICE AND RELATED METHODS

RELATED APPLICATIONS

This application claims benefit of U.S. Provisional Patent Application No. 63/038,587, filed on Jun. 12, 2020, entitled CATHETER PLACEMENT DEVICE AND RELATED METHODS, which is incorporated herein in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion. Placement of the needle and the catheter within the vein can be difficult for the clinician. In some instances, the clinician may make multiple attempts to locate a vein and may make multiple needle sticks, which may damage a body of the patient and increase anxiety in the patient.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to an intravenous (IV) therapy system to facilitate the insertion of a catheter or another suitable IV device into a patient. In some embodiments, the IV therapy system may include a band, which may include a collar. In some embodiments, the band may be made of flexible material to be secured around a limb of a patient. In some embodiments, the IV therapy system may include a window formed through the band to provide access to the patient's body. In some embodiments, the IV therapy system may include a tourniquet formed within the band to selectively apply a pressure against the patient's body. In some embodiments, the IV therapy system may include a blood vessel indicator to indicate where the catheter or other suitable IV device is to be inserted.

In some embodiments, the band may include a processor to control a number of mechanical and electrical devices of the band. In some embodiments, the processor may control the pressure applied to the patient's body via the tourniquet placed within the band of the band. In some embodiments, the tourniquet may include a bladder formed within the band of flexible material and such that the bladder is inflated and deflated to create a pulsating pattern of pressure against the patient's body.

In some embodiments, the band may include a magnetic device to secure the catheter or other suitable IV device to the band to stabilize the catheter or other suitable IV device. The magnetic device may be a permanent magnetic device or an electromagnetic device. In some embodiments, the band may include a sealing lip to interface with a protective medical dressing to prevent contamination at an injection site created upon insertion of the catheter or other suitable IV device into the patient's body.

In some embodiments, the blood vessel indicator includes a near-infrared (near-IR) camera to detect the location of the blood vessel within the patient's body. In some embodiments, a mechanical channel may be formed in the blood vessel indicator to direct the catheter or other suitable IV device to the location of a blood vessel within the patient's body.

In some embodiments, the band may include an IV device insertion indicator to indicate the insertion of the catheter or other suitable IV device into the patient's blood vessel. In some embodiments, the band may include an infusion status indicator indicating the status of an infusion of fluid through the catheter or other suitable IV device and into the patient's blood vessel.

It is to be understood that both the foregoing general description and the following detailed description is examples and explanatory and are not restrictive of the present disclosure. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 5 is a flowchart illustrating an example method of forming the band according to some embodiments of the present disclosure.

DESCRIPTION OF EMBODIMENTS

As used in the present disclosure, the term "distal" refers to a portion of an intravenous therapy system that is farther from a user, and the term "proximal" refers to a portion of the intravenous therapy system that is closer to the user. Thus, for example, an end of a catheter first touching the body of the patient is a distal end of the catheter, while an opposite end of the catheter is a proximal end of the catheter. As used in the present disclosure, the term "user" may refer to a clinician, doctor, nurse, or any other care provider and may include support personnel.

As used herein, the term "top", "up" or "upwardly" refers to a location on the needle of this intravenous therapy system that, during use, is radially away from the longitudinal axis of the intravenous therapy system and away from the patient's skin. Conversely, as used herein, the term "bottom", "down" or "downwardly" refers to a location on the needle of this intravenous therapy system that, during use, is radially away from the longitudinal axis of the intravenous therapy system and toward the patient's skin.

As used herein, the term "in" or "inwardly" refers to a location with respect to the needle of this intravenous therapy system that, during use, is toward an inside of the intravenous therapy system. Conversely, as used herein, the term "out" or "outwardly" refers to a location with respect to the needle of this intravenous therapy system that, during use, is toward an outside of the intravenous therapy system.

Although the embodiments described herein are used in connection for use as an intravenous therapy system to receive a blood sample or introduce a medicament into the body of a patient, it is to be understood that this intravenous therapy system is applicable to other medical devices where it is desirable for a needle and/or catheter to be inserted into a blood vessel of a patient.

Figure 1:
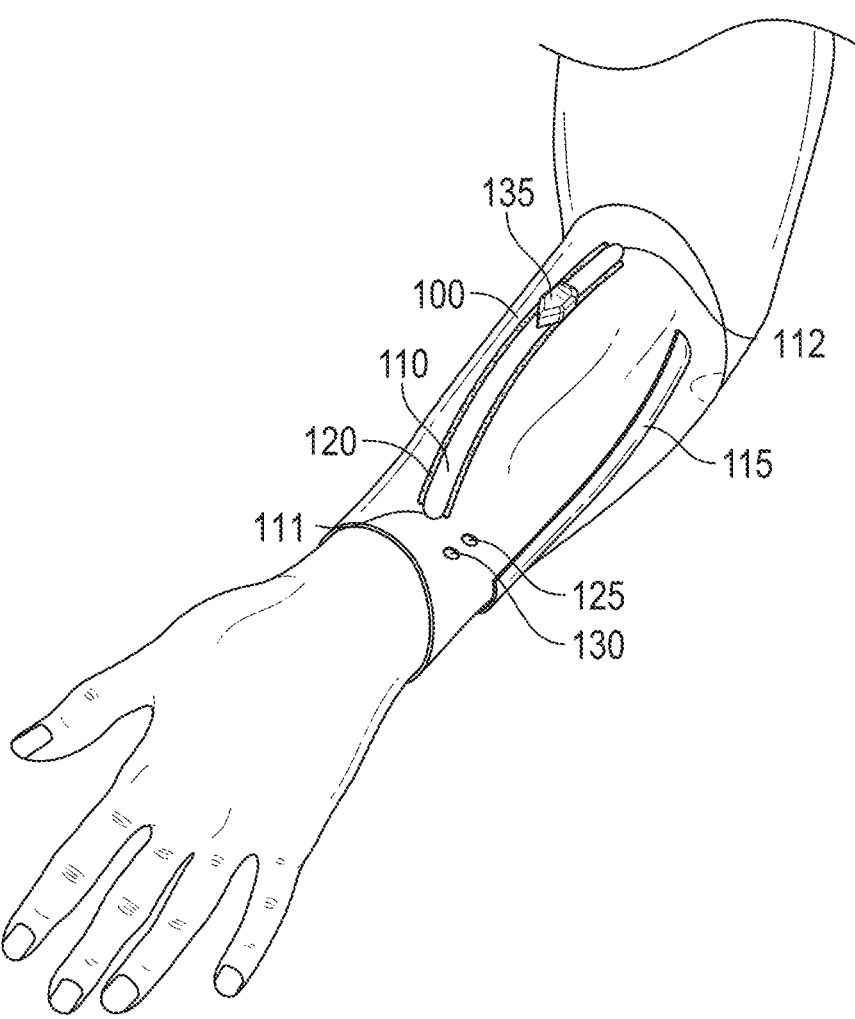
FIG. 1 is a perspective view of an example band according to some embodiments of the present disclosure.

FIG. 1 is a perspective view of a band 100 according to some embodiments of the present disclosure. In some embodiments, an intravenous therapy system may include the band 100. Although FIG. 1 shows the band 100 as a device configured to interface with an arm of a patient, the present specification contemplates that the band 100 may be used to interface with any portion of the patient's body including a leg, a torso, etc. For example, the band 100 may extend around or be coupled to the portion of the patient's body. The present specification, therefore, contemplates that other sizes and/or arrangements of the band 100 may be used to accomplish the functionalities of the band 100 described in the present disclosure. In some embodiments, the band 100 may include an armband.

In some embodiments, the band 100 may be made of any flexible or elastomeric material. In some embodiments, the band 100 may include a collar or sleeve that may encircle a patient's limb such as an arm. In some embodiments, the band 100 may partially surround the patient's limb. The material may, in some embodiments, may remain flush against or in contact with the patient's arm during use of the band 100. In these and other embodiments, the material may include a polychloroprene rubber, which may facilitate contact with the patient's arm. In some embodiments, the material may include any type of elastic material that causes the band 100 to remain flush against the patient's body during use of the band 100.

In some embodiments, the band 100 may further include a window 110 formed through a portion of the band 100. In some embodiments, the window 110 may be placed at a location on the band 100 that would provide a clinician implementing an intravenous (IV) device to access the surface of the patient's body for insertion of the IV device. In some embodiments, the window 110 may be placed at a location through the band 100 where, when the band 100 is worn by the patient, a blood vessel such as a vein is centered within or otherwise accessible through the window 110 by the IV device. The window 110 may include a proximal end 111 and a distal end 112.

In some embodiments, the window 110 may include an elongated slit formed through the band 100 that follows a path where, according to human anatomy, a blood vessel would be. For example, where the band 100 is to be worn by a patient on the patient's left arm, the window 110 may be formed through the band 100 at a location of a radial artery, an ulnar artery, a posterior interosseous artery, a common interosseous artery, a brachial artery, a cephalic vein, a median vein, a basilic vein, a median basilic vein, a cephalic vein, a basilic vein, or another artery or vein are located within the patient's body. In some embodiments, the material of the band 100 may include an elastic and flexible material, a pressure may be applied at the window 110, which may result in the blood vessel to be more pronounced within the window 110. It should be understood that, although FIG. 1 shows a specific location of the window 110 formed through the band 100, the present specification contemplates various lengths, widths, and placements of the window 110.

In some embodiments, the window 110 may be proximate one or more magnetic elements 120. In the embodiments, the magnetic elements 120 may be electromagnetic elements or permanent magnets. In the embodiment where the magnetic elements 120 are electromagnetic elements, the magnetic elements 120 may be electrically coupled to a power source that allows for the selective magnetization of the magnetic elements 120 either in a magnetized state or demagnetized state. In some embodiments, the magnetic elements 120 may facilitate placement of other medical devices against the band 100 that may be used to provide care to the patient. In some embodiments, the magnetic elements 120 may stabilize an IV device against the band 100 so that the insertion quality of the IV device is maintained while, for example, the clinician attends to other tasks related to care of the patient. Although the present specification describes the magnetic elements 120, the present specification contemplates that another type of suitable securing device may be used and is not limited to the use of the magnetic elements 120 described in the present disclosure.

In some embodiments, the band 100 may include a blood vessel indicator 135 disposed within the window 110. In some embodiments, the blood vessel indicator 135 may provide a visual indicator to a clinician as to where, for example, an IV device is to be inserted into the patient's body so as to intersect with a blood vessel. In some embodiments, as described in the present disclosure, the blood vessel indicator 135 may include a near-infrared (near-IR) camera that detects the location of a blood vessel. In this embodiment, the near-IR camera may detect whether the blood vessel is an artery or vein and provide feedback (e.g., visual feedback via a light-emitting diode or audible feedback via a speaker) to the clinician as to where a blood vessel is indicated.

In some embodiments, the blood vessel indicator 135 may be magnetically coupled to the band 100 via the magnetic elements 120 at a location aligned with the blood vessel in response to the blood vessel being detected. In some embodiments, as illustrated in FIG. 1, the blood vessel indicator 135 may include a pointed tip that provides a visual indicator to the clinician as to a location on the patient's body where the IV device should be inserted in order to gain access to a blood vessel within the patient's body.

In some embodiments, the window 110 may further include any protective medical dressing (not illustrated) used to prevent contamination of an injection site of an IV device. In some embodiments, the window 110 may include a sealing lip or other type of gasket that interfaces directly and sealably with the protective medical dressing such that the protective medical dressing is not adhered to the patient's body. In some embodiments, the sealing lip may allow the protective medical dressing to be suspended across the window 110 thereby preventing contamination at the IV device injection site as well as between the band 100 and the patient's body.

In some embodiments, the band 100 may include a tourniquet 115, which may be coupled to or disposed within the band 100. In some embodiments, the tourniquet 115 may be any device that selectively compresses an artery or vein. In relation to an IV device being injected into the patient's body, the tourniquet 115 may be used to inhibit the flow of blood through the blood vessel, thereby making the blood vessel more prominent and accessible for injection of the IV device into the blood vessel. In some embodiments, the tourniquet 115 may include a bladder placed between an outer surface and inner surface of the flexible material of the band 100.

In some embodiments, the tourniquet 115 may be digitally controlled so that an amount of air or other fluid is pneumatically introduced into the tourniquet 115 at specific intervals. For example, the tourniquet 115 may be sequentially inflated and deflated within the band 100 so that a pulsating pressure along a length of the band 100 is produced in order to improve vein identification within the window 110 formed through the band 100. In some embodiments, the tourniquet 115 may be digitally coupled to a processor that directs the introduction of air or other fluids into the tourniquet 115 to achieve any pattern of inflation and deflation of the tourniquet 115 as described in the present disclosure. As described in the present disclosure, the processor (not illustrated) may be used to execute computer readable program code to activate other devices associated with the band 100 as described in the present disclosure, the magnetic elements 120 being one example.

In some embodiments, the band 100 may include an IV device insertion indicator 125, such as, for example, an IV catheter insertion indicator. In some embodiments, the IV device insertion indicator 125 may indicate to a clinician that an IV device is inserted correctly into a blood vessel of the patient. In some embodiments, in order to detect the placement of the IV device, the processor may implement a metal detector (not illustrated) or the near-IR camera of the blood vessel indicator 135. In some embodiments, by receiving the data from these detection devices, the processor may provide feedback, in real-time for example, to the clinician via the IV device insertion indicator 125. In some embodiments, the IV device insertion indicator 125 may be a light-emitting diode (LED) or series of LEDs or another suitable light that indicates visually to a clinician whether the IV device has apparently been inserted correctly into the patient's blood vessel. In some embodiments, the IV device insertion indicator 125 may be a speaker that indicates audibly to a clinician whether the IV device has apparently been inserted correctly into the patient's blood vessel.

In some embodiments, the band 100 may include an infusion status indicator 130. The infusion status indicator 130 may provide a visual or audible indicator to a clinician as to the status of an infusion or other fluidic status of the IV device inserted into the patient's vein. In some embodiments, the near-IR camera or some other fluidic detection device may be coupled to the processor of the band 100 such that data descriptive of fluids passing through the IV may be received and relayed to the infusion status indicator 130 notifying the clinician of a status of an infusion, a blood draw, or other fluids passing through the IV device. In some embodiments, the infusion status indicator 130 may include a light-emitting diode (LED) or series of LEDs that indicates visually to a clinician a current status of an infusion, blood drawn, or the presence of fluids within the IV device. In some embodiments, the infusion status indicator 130 may include a speaker that indicates audibly to a clinician a current status of an infusion, blood drawn, or the presence of fluids within the IV device.

In some embodiments, the band 100 may enable smart tourniquet behavior that better highlights blood vessels and blood vessel features more clearly for the clinician to access those blood vessels. After insertion of an IV device, the band 100 may couple with the IV device to provide rapid stabilization of the IV device relative to the patient's body. This stabilization may play a role in preserving the initial placement quality of the IV device. In some embodiments, the band 100 may be used as the data and power base station for, for example, a digital catheter. In this embodiment, the band 100 may reduce the hardware burden on the IV device thereby minimizing associated size and cost of the IV device and those devices used to infuse fluids into a patient's body or receive blood samples from the patient.

In some embodiments, the band 100 may contain physiological or environmental sensors such as the IV device insertion indicator 125 and infusion status indicator 130. These sensors may work independently or in conjunction with other IV device-based sensors to assess patient condition, infusion state, unscheduled infusions, flush events among many other indications. This increases the functionality of the band 100 such that the clinician may know more about the patient at one location than otherwise realized. Instead of a clinician is left to interact with multiple devices in order to bring together a piece-meal network of products to provide similar care realized via the use of the band 100 described in the present disclosure. By bringing the features of the band 100 described in the present disclosure together into a single device will simplify workflows, increase insertion and tip placement confidence of an IV device while also reducing complications related to the use of the other myriad numbers of devices. Still further, the band 100 described in the present disclosure may reduce storage costs of the other multiple devices used to perform the functions of the band 100 described in the present disclosure.

In some embodiments, the band 100 may also reduce a need for an adhesive-based IV device dressing. As described, the sealing lip on the band 100 may interface directly with a protective medical dressing to create a closed or near-closed environment at the injection site of the IV device.

Certain features, such as the digital tourniquet 115 of the band 100, may offer unique opportunities to improve on existing infusion or blood draw techniques. With some tourniquet devices, pressure is not dynamic. However, with the tourniquet 115 of the band 100 described in the present disclosure, a pulsating pressure may be placed along a length of the band 100 thereby further improving blood vessel identification. Additionally, as point-of-care sensors improve in functionality, the presently-described band 100 may be coupled directly to these improved sensors to enable still further improved functionality of the band 100.

Figure 2:
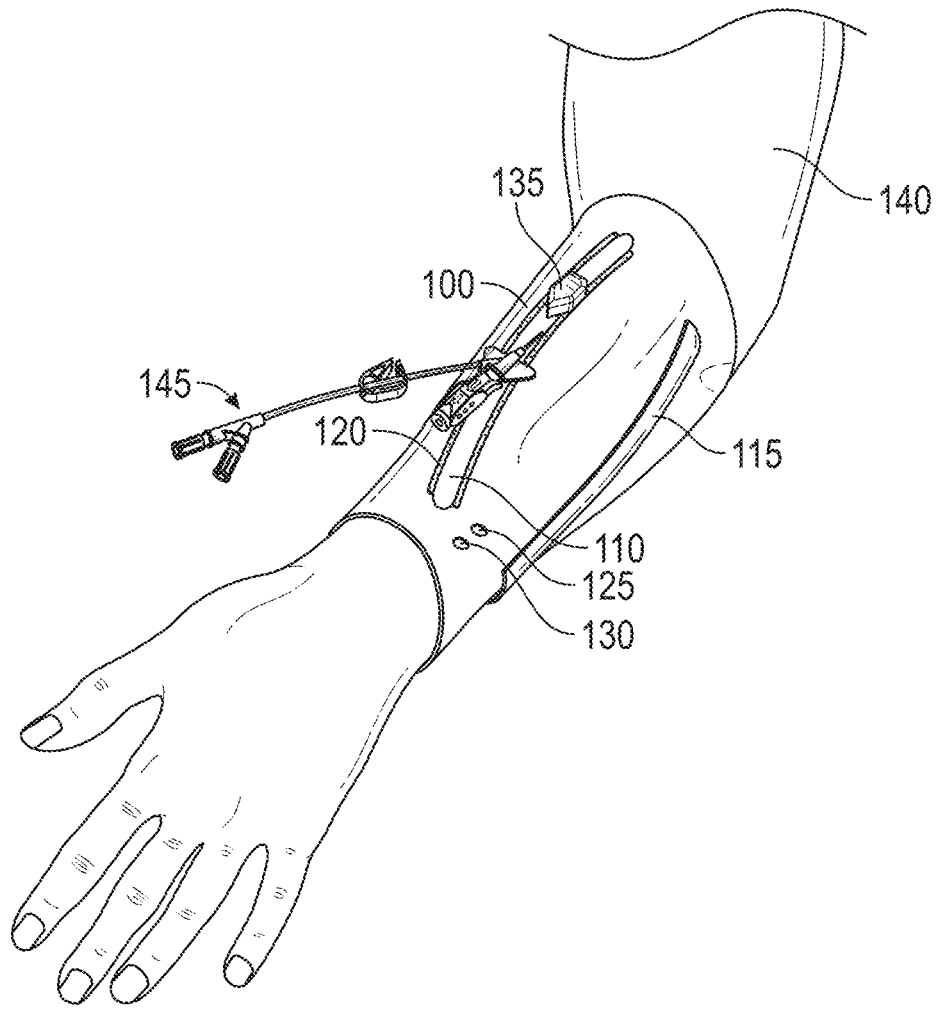
FIG. 2 is a perspective view of the band and an example catheter system, according to some embodiments of the present disclosure.

FIG. 2 is a perspective view of the IV therapy system that may include the band 100 according to some embodiments of the present disclosure. In FIG. 2, the band 100 is illustrated to be interfacing with the IV device 145. In some embodiments, the IV device 145 may include a catheter device, which may include a catheter adapter coupled to a catheter. In some embodiments, the catheter may include a peripheral intravenous catheter (PIVC), a midline catheter, or a peripherally-inserted central catheter. In some embodiments, the IV device 145 may be any type of IV device 145 that allows a clinician to gain fluidic access to a blood vessel within a patient's body. In some embodiments, the IV device 145 may include a port to receive a blood sample from the patient's blood vessel. In some embodiments, the port or another port of the IV device 145 may be used by the clinician to infuse one or more infusing fluids, such as normal saline solution, various medicaments, and total parenteral nutrition into the patient's blood vessel.

In some embodiments, during operation of the band 100, a clinician may secure the band 100 around the limb of the patient. In the example illustrated in FIG. 2, the band 100 has been secured around a left arm 140 of the patient. In some embodiments, the band 100 may be placed on the patient's arm such that the blood vessel may be accessed through the window 110 formed through the band 100.

In some embodiments, in response to the window 110 being situated over a blood vessel, the clinician may use the blood vessel indicator 135 to determine an exact location of the blood vessel within the patient's body along the window 110. In some embodiments, the clinician may use the IV device insertion indicator 125 that includes a near-IR camera that detects the location of a blood vessel within the patient's body. In some embodiments, the IV device insertion indicator 125 may further include the tip that would indicate visually to the clinician a point along the patient's body where the IV device 145 should be inserted into the patient's body to gain fluidic access to the blood vessel tin the present disclosure.

In some embodiments, during insertion, the clinician may pass the IV device 145 through a protective medical dressing that is held across the window 110 via the sealing lip or other type of gasket around the window 110. In some embodiments, the protective medical dressing may prevent contamination of the injection site created by the insertion of the IV device 145 into the patient's body.

In some embodiments, during operation, the tourniquet 115 of the band 100 may also be activated to inhibit the flow of blood through, for example, superficial veins thereby making those veins more prominent and accessible for the injection of the IV device 145. In some embodiments, activation of the tourniquet 115 may include passing air or other fluids into a bladder of the tourniquet 115 so that the blood flow at or around the tourniquet 115 may be inhibited from passing. In some embodiments, the tourniquet 115 may be sequentially inflated and deflated within the band 100 so that a pulsating pressure along the length of the band 100 is produced in order to improve vein identification within the window 110 formed through the band 100. The activation of the tourniquet 115, in some embodiments, may be accomplished via the use of a processor that detects an activation signal from, for example, a clinician actuating a button, and causes the fluids to pass into the bladder of the tourniquet 115. This activation of the tourniquet 115 may be conducted prior to the insertion of the IV device 145 into the patient's body, prior to the clinician's attempts to detect the presence of a blood vessel with the IV device insertion indicator 125, or at any other time during the operation of the band 100 as would be necessary to facilitate the insertion of the IV device 145.

In some embodiments, after the IV device 145 has been inserted into the blood vessel, the processor of the band 100 may also receive input from a number of sensors descriptive of the insertion of the IV device 145, the placement of the IV device 145, and the occurrence of an infusion or blood draw via the IV device 145. These sensors may include, among others, the near-IR camera of the blood vessel indicator 135, a metal detector formed on the blood vessel indicator 135 or other portion of the band 100, a heart rate sensor, a blood-oxygen level sensor (e.g., oximeter), and a fluidic flow detector, among other types of sensors. In some embodiments, the processor may then receive this data and provide output to a clinician at the infusion status indicator 130 and IV device insertion indicator 125, for example, providing feedback to the clinician as to the current status of the patient, the IV device 145 and the band 100.

In some embodiments, during operation and after the clinician has inserted the IV device 145 into the patient's blood vessel, the clinician may secure the IV device 145 to the band 100. In some embodiments, the magnetic elements 120 formed around the window 110 may be used to secure the IV device 145 to the band 100. In some embodiments, the IV device 145 may include certain ferromagnetic elements that may interact with the magnetic elements 120 so that the clinician can secure the IV device 145 to the band 100. In some embodiments, the processor may be electrically coupled to a power source and an electromagnet serving as the magnetic elements 120 such that a voltage may be applied to the magnetic elements 120 causing the electromagnet to be magnetized. This allows the clinician to selectively determine when the IV device 145 should and should not be magnetically coupled to the band 100 such as during insertion and after use of the IV device 145.

Figure 3:
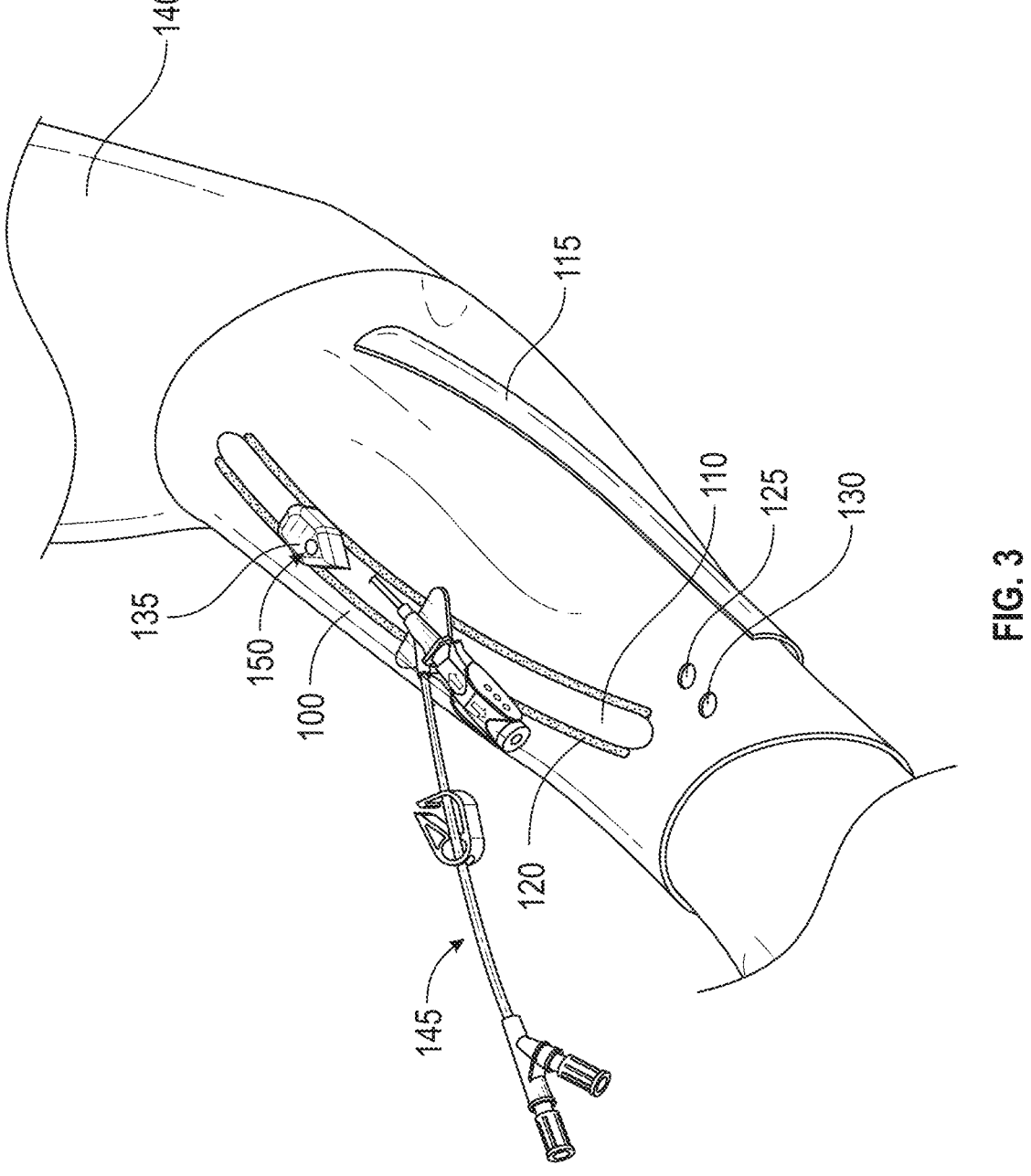
FIG. 3 is a perspective view of the band and the catheter system according to some embodiments of the present disclosure.

FIG. 3 is a perspective view of the band 100 according to some embodiments of the present disclosure. FIG. 3 shows a relatively closer view of the band 100 than that illustrated in FIGS. 1 and 2. Again, the band 100 show in FIG. 3 includes similar elements as those presented in connection with FIGS. 1 and 2.

In FIG. 3, the band 100 is illustrated to include additional features of the blood vessel indicator 135, according to some embodiments. In some embodiments, the blood vessel indicator 135 may include an aperture 150 formed through the blood vessel indicator 135. In some embodiments, the aperture 150 may be used as another mechanism by which the clinician may insert the IV device 145 into the patient's body. Although FIG. 3 shows the IV device 145 being inserted into the patient's body in front of the blood vessel indicator 135, another method may be used to insert the IV device 145 into the patient's body through the aperture 150. In these embodiments, the clinician may access the blood vessel by placing, coaxially, a needle and/or catheter into the aperture 150 of the blood vessel indicator 135. This may allow for some types of IV devices 145 to be used to access the blood vessel at a more perpendicular angle relative to the patient's body. In some embodiments, the aperture 150 angled through the blood vessel indicator 135 so that various angles may be provided to various other types of IV devices 145. Again, the blood vessel indicator 135 may implement the presence of the blood vessel using, for example, a near-IR camera formed within the blood vessel indicator 135 as described in the present disclosure.

Figure 4:
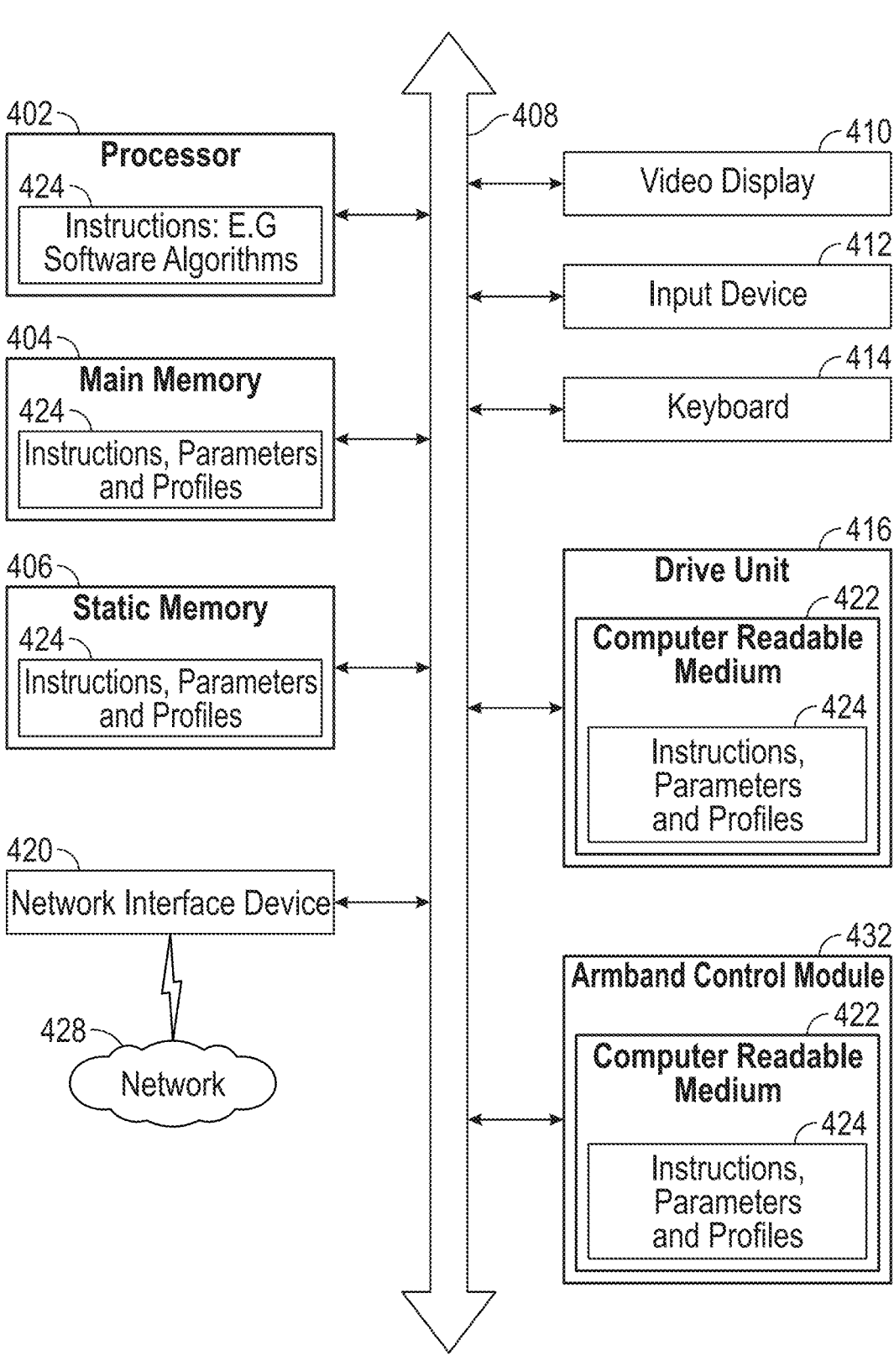
FIG. 4 is a block diagram of the band according to some embodiments of the present disclosure.

FIG. 4 is a block diagram of the band 100 according to some embodiments of the present disclosure. As described in the present disclosure, the band 100 may include various electrical components that allows the band 100 to engage in the functionalities of the band 100 described in the present disclosure. Although, in specific examples, the band 100 may be described as "including" certain elements, the present specification contemplates that the elements illustrated in FIG. 4 and described in the present disclosure may be operatively coupled to the band 100 whether those elements form a physical part of the band 100 itself or form part of, for example, a computing device communicatively coupled to the band 100. As such, the present specification contemplates that any of the elements illustrated in FIG. 4 and described in the present disclosure, may be part of the resources provided to the band 100 and distributed over a network of devices and/or may be physically coupled to the band 100 itself during operation of the band 100.

The band 100 may include a processor 402 such as a central processing unit (CPU), control logic or some combination of the same. Any of the processing resources may operate to execute code in the form of instructions 424 that is either firmware or software code. Moreover, the band 100 may include memory such as main memory 404, static memory 406, computer readable medium 422 storing instructions 424, and drive unit 416 (volatile (e.g. random-access memory, etc.), nonvolatile (read-only memory, flash memory etc.) or any combination thereof). The band 100 may also include one or more buses 408 operable to transmit communications between the various hardware components such as any combination of various input and output (I/O) devices that may be associated with the band 100.

In some embodiments, the band 100 may include a network interface device of 420 to provide connectivity to a network 428, e.g., a wide area network (WAN), a local area network (LAN), wireless local area network (WLAN), a wireless personal area network (WPAN), a wireless wide area network (WWAN), or other networks. Connectivity to the network 428 by the band 100 may be via wired or wireless connection. In some embodiments, the network interface adapter 420 may operate in accordance with any wireless data communication standards. To communicate with a wireless local area network, standards including IEEE 802.11 WLAN standards, IEEE 802.15 WPAN standards, WWAN such as 3GPP or 3GPP2, or similar wireless standards may be used.

The network interface device 420 may be used to communicatively couple components of the band 100 with, for example, computing devices that include other processing resources, a video display 410, an input device 412, and a keyboard 414. As such, the band 100 may be able to wireless transmit data to the processor 402 of the computing device so that the processor may receive the data and provide output per executed instructions 424 stored on the computing device.

The band 100 may include a band control module 432. In some embodiments, the band control module 432 may in the form of executed computer readable program code executable by the processor 402. In some embodiments, the band control module 432 may be an integrated circuit (such as an Application Specific Integrated Circuit (ASIC), a Field Programmable Gate Array (FPGA), a structured ASIC, or a device embedded on a larger chip), a card (such as a Peripheral Component Interface (PCI) card, a PCI-express card, a Personal Computer Memory Card International Association (PCMCIA) card, or other such expansion card), or a system (such as a motherboard, a system-on-a-chip (SoC), or a stand-alone device).

The band control module 432 may receive input from any sensor of the band 100 described in the present disclosure and cause that data to be processed by the processor 402. By way of example, the band control module 432 may receive input, data, or other type of information from the blood vessel indicator 135 descriptive of a location of a blood vessel within the patient's body. During operation of the band 100, the blood vessel indicator 135 may provide data descriptive of whether the blood vessel indicator 135 has been placed over or near a blood vessel. The band control module 432 may then, with the processor 402, cause the processor 402 to execute computer readable code to determine when the blood vessel indicator 135 has indicated that a blood vessel has been detected. In an example, the processor 402 may cause an indicator either on the band 100 or at a communicatively coupled computing device to indicate to the clinician that the blood vessel indicator 135 has been placed close to or over a blood vessel. The clinician may then secure the blood vessel indicator 135 to the band 100 via, for example, the magnetic elements 120 described in the present disclosure.

In another embodiment, the band control module 432 may receive data from a metal detector or other sensor that monitors the placement of an IV device 145 within the patient's body. When the band control module 432 receives this data, it may, with the processor 402 cause an indication to be provided to the user via, for example, the IV device insertion indicator 125, to indicate that the IV device 145 has been placed correctly within the patient's blood vessel.

In some embodiments, the band control module 432 may receive input from a fluid flow sensor associated with the IV device 145 indicating that fluid is passing through the fluidic paths formed within the IV device 145. The band control module 432 may then, with the processor 402, determine when a fluid is flowing through the IV device 145 and cause the processor 402 to signal to an infusion status indicator 130 to indicate that an infusion is in process. The band control module 432 may cause any associated instructions, parameters, and profiles to be executed by the processor 402 in order to cause input from any of a number of sensors to be processed and output presented to the clinician in order to facilitate in the functionalities of the band 100 described in the present disclosure.

In some embodiments, the band 100 may also include any power source used to power the devices described in the present disclosure. The power source may include a battery pack (not illustrated) that is electrically coupled to the processor 402 and band control module 432 so that signals may be sent to the components of the band 100 as described in the present disclosure.

FIG. 5 is a flowchart illustrating a method 500 of forming a band according to some embodiments of the present disclosure. The method 500 may include, at block 505, forming a collar of flexible material to be secured to the limb of a patient. In some embodiments, the flexible material may be made of any type of elastic material that causes the band to remain flush against the patient's body during use of the band.

The method 500 may further include, at block 510, forming a window through the collar to provide access to the patient's body. The window may be placed at a location on the collar that would provide a clinician implementing an intravenous (IV) device to access the surface of the patient's body for insertion of the IV device. In some embodiments, the window may be placed at a location through the collar of the band where, when the band is worn by the patient, a blood vessel such as a vein is centered or otherwise accessible through the window by the IV device.

The method 500 may also include forming a tourniquet within the collar to selectively apply a pressure against the patient's body at block 515. The tourniquet may be any device that selectively compresses an artery or vein. In relation to an IV device being injected into the patient's body, the tourniquet may be used to inhibit the flow of blood through, for example, superficial veins thereby making those veins more prominent and accessible for the injection of the IV device. In some embodiments, the tourniquet may be placed within the collar of the band at a location where the blood flow of a vein or other blood vessel positioned within the window may be temporarily inhibited so that that vein within the window is rendered more prominent. In some embodiments, the tourniquet may be in the form of a bladder placed between an outer surface and inner surface of the flexible material of the collar.

The method 500 may include, at block 520, forming a blood vessel indicator to indicate where the Catheter or other suitable IV device is to be inserted. In some embodiments, as described in the present disclosure, the blood vessel indicator may include a near-infrared (near-IR) camera that detects the location of a blood vessel. In this embodiment, the near-IR camera may detect whether the blood vessel is an artery or vein and provide feedback (e.g., visual feedback via a light-emitting diode or audible feedback via a speaker) to the clinician as to where a blood vessel is indicated.

The method 500 may include communicatively coupling the tourniquet to a processor to direct the application of pressure against the patient's body at block 525. Additionally, the blood vessel indicator, the IV device insertion indicator, the infusion status indicator, and any associated sensors described in the present disclosure may be communicatively coupled to the processor via the band control module as described in the present disclosure.

Again, it is understood that the embodiments of the present application may be combined. As an example, the embodiments of FIGS. 1-5 may be arranged to fit specific uses based on the type of action being conducted.

The presently described in the present disclosure may provide for clinicians to roughly highlight a targeted blood vessel using the window formed through the collar while highlighting the insertion site with a blood vessel indicator. These "landing pad" features are not objective, and the clinician may use these features to isolate a targeted blood vessel. The band may enable smart tourniquet behavior that better highlights blood vessels and blood vessel features more clearly for the clinician to access those blood vessels. After insertion of an IV device, the band may couple with the IV device and/or an adapter of the IV device to provide rapid stabilization of the IV device relative to the patient's body. This stabilization may play a role in preserving the initial placement quality of the IV device. In some embodiments, the band may be used as the data and power base station for, for example, a digital catheter. In this embodiment, the band may reduce the hardware burden on the IV device thereby minimizing associated size and cost of the IV device and those devices used to infuse fluids into a patient's body or receive blood samples from the patient.

In some embodiments, the band may contain physiological or environmental sensors such as the IV device insertion indicator and infusion status indicator. These sensors may work independently or in conjunction with other IV device-based sensors to assess patient condition, infusion state, unscheduled infusions, flush events among many other indications. This increases the functionality of the band such that the clinician may know more about the patient at one location than otherwise realized. Instead of a clinician is left to interact with multiple devices in order to bring together a piece-meal network of products to provide similar care realized via the use of the band described in the present disclosure. By bringing the features of the band described in the present disclosure together into a single device will simplify workflows, increase insertion and tip placement confidence of an IV device while also reducing complications related to the use of the other myriad numbers of devices. Still further, the band described in the present disclosure may reduce storage costs of the other multiple devices used to perform the functions of the band described in the present disclosure.

In some embodiments, the band may also eliminate the need for an adhesive-based IV device dressing. As described, the sealing lip on the band may interface directly with a protective medical dressing to create a closed or near-closed environment at the injection site of the IV device.

Certain features, such as the digital tourniquet of the band, may offer unique opportunities to improve on existing infusion or blood draw techniques. With some tourniquet devices, pressure is not dynamic. However, with the tourniquet of the band described in the present disclosure, a pulsating pressure may be placed along a length of the band thereby further improving blood vessel identification. Additionally, as point-of-care sensors improve in functionality, the presently-described band may be coupled directly to these improved sensors to enable still further improved functionality of the band.

All examples and conditional language recited in the present disclosure are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. A band to facilitate the insertion of a catheter into a patient, comprising:
   a sleeve made of flexible material, wherein the sleeve has a cylindrical shape and is configured to be secured around a limb of a patient;
   wherein an elongated window is formed in and through the flexible material of the sleeve to provide access to the limb of the patient through the sleeve, wherein the elongated window comprises a distal end and a proximal end, wherein a length of the elongated window between the distal end and the proximal end is greater than a width of the elongated window to follow a path of a blood vessel in the limb of the patient, wherein the flexible material in and through which the elongated window is formed is configured to apply pressure around the path of the blood vessel to cause the blood vessel to be more pronounced within the elongated window;
   a tourniquet formed within a portion of the flexible material of the sleeve to selectively apply a pressure against the limb of the patient, wherein the tourniquet comprises a bladder, wherein the bladder comprises an elongated strip having a width and a length longer than the width, wherein the portion of the flexible material of the sleeve in which the tourniquet is formed extends generally parallel to a longitudinal axis of the sleeve and generally parallel to the elongated window, wherein the bladder is configured to be sequentially inflated and deflated along the length of the bladder to thereby correspondingly and sequentially increase and decrease a pressure applied by the portion of the flexible material of the sleeve to the limb of the patient; and a blood vessel indicator to indicate where the catheter is to be inserted, wherein the blood vessel indicator comprises a near-infrared (near-IR) camera disposed within the elongated window to detect the blood vessel within the elongated window, wherein the near-infrared camera is disposed closer to a distal end of the elongated window than a proximal end of the elongated window to facilitate placement of the catheter proximal to the near-infrared camera.

2. The band of claim 1, further comprising a processor that controls the tourniquet.

3. The band of claim 2, wherein the processor is configured to cause the bladder to be inflated and deflated to create a pulsating pattern of pressure against a body of the patient.

4. The band of claim 1, further comprising a magnetic element integrated into the flexible material of the sleeve and extending along the length of the elongated window to selectively couple the catheter to the sleeve to stabilize the catheter.

5. The band of claim 1, further comprising a sealing lip integrated into the flexible material of the sleeve to interface with a protective medical dressing to prevent contamination at an injection site created upon insertion of the catheter into the patient's body.

6. The band of claim 1, further comprising a mechanical channel formed in the blood vessel indicator to direct the catheter to a location of the blood vessel within the patient's body.

7. The band of claim 1, further comprising an IV device insertion indicator integrated into the flexible material of the sleeve to indicate the insertion of the catheter into the blood vessel.

8. The band of claim 1, further comprising an infusion status indicator integrated into the flexible material of the sleeve indicating the status of an infusion of fluid through the catheter and into the blood vessel.

9. The band of claim 1, further comprising a processor digitally coupled to the bladder, wherein the processor directs introduction of air or another fluid into the bladder to achieve a particular pattern of inflation or deflation of the bladder.

10. A method of manufacturing a band for use in inserting a catheter into a patient, the method comprising:

forming a sleeve of flexible material, wherein the sleeve has a cylindrical shape and is configured to be secured around a limb of a patient;

forming an elongated window in and through the flexible material of the sleeve to provide access to the limb of the patient through the sleeve, wherein the elongated window comprises a distal end and a proximal end, wherein a length of the elongated window between the distal end and the proximal end is greater than a width of the elongated window to follow a path of a blood vessel in the limb of the patient, wherein the flexible material in and through which the elongated window is formed is configured to apply pressure around the path of the blood vessel to cause the blood vessel to be more pronounced within the elongated window;

forming a tourniquet within a portion of the flexible material of the sleeve to selectively apply a pressure against the limb of the patient, wherein the tourniquet comprises a bladder, wherein the bladder comprises an elongated strip having a width and a length longer than the width, wherein the portion of the flexible material of the sleeve in which the tourniquet is formed extends generally parallel to a longitudinal axis of the sleeve and generally parallel to the elongated window, wherein the bladder is configured to be sequentially inflated and deflated along the length of the bladder to thereby correspondingly and sequentially increase and decrease a pressure applied by the portion of the flexible material of the sleeve to the limb of the patient; and integrating a blood vessel indicator into the flexible material of the sleeve to indicate where the catheter is to be inserted; and communicatively coupling the tourniquet to a processor to direct the application of pressure against the patient's body, wherein the bladder is configured to be sequentially inflated and deflated along the length of the bladder when the processor detects an activation signal generated in response to input from a clinician.

11. The method of claim 10, wherein the bladder is inflated and deflated, via direction of the processor, to create a pulsating pattern of pressure against the patient's body.

12. The method of claim 10, further comprising integrating a magnetic device into the flexible material and by the elongated window to couple the catheter to the sleeve to stabilize the catheter.

13. The method of claim 10, further comprising integrating a sealing lip into the flexible material to interface with a protective dressing to prevent contamination at an injection site created upon insertion of the catheter into the patient's body.

14. The method of claim 10, further comprising forming a mechanical channel in the indicator to direct the catheter to the location of the blood vessel within the patient's body.

15. The method of claim 14, forming a near-infrared (near-IR) camera within the indicator to detect the location of the blood vessel within the patient's body.

16. The method of claim 10, further comprising integrating a light-emitting diode (LED) into the flexible material to provide a visual indication of the insertion of the catheter into the blood vessel.

17. The method of claim 10, further comprising integrating an LED into the flexible material to provide a visual indication as to a status of an infusion of fluid through the catheter and into the blood vessel.

18. A band to facilitate the insertion of a catheter into a patient, comprising:

a sleeve made of flexible material, wherein the sleeve has a cylindrical shape and is configured to be secured around a limb of a patient;

wherein an elongated window is formed in and through the flexible material of the sleeve to provide access to the limb of the patient through the sleeve, wherein the elongated window comprises a distal end and a proximal end, wherein a length of the elongated window between the distal end and the proximal end is greater than a width of the elongated window to follow a path of a blood vessel in the limb of the patient, wherein the flexible material in and through which the elongated window is formed is configured to apply pressure around the path of the blood vessel to cause the blood vessel to be more pronounced within the elongated window;

a tourniquet formed within a portion of the flexible material of the sleeve to selectively apply a pressure against the limb of the patient, wherein the tourniquet comprises a bladder, wherein the bladder comprises an elongated strip having a width and a length longer than the width, wherein the portion of the flexible material of the sleeve in which the tourniquet is formed extends generally parallel to a longitudinal axis of the sleeve and generally parallel to the elongated window, wherein the bladder is configured to be sequentially inflated and deflated along the length of the bladder to thereby correspondingly and sequentially increase and decrease a pressure applied by the portion of the flexible material of the sleeve to the limb of the patient;

a processor integrated into the flexible material of the sleeve, the processor being configured to control the tourniquet;

a blood vessel indicator to indicate where the catheter is to be inserted, wherein the blood vessel indicator comprises a near-infrared (near-IR) camera disposed within the elongated window to detect the blood vessel within the elongated window, wherein the near-infrared camera is disposed closer to a distal end of the elongated window than a proximal end of the elongated window to facilitate placement of the catheter proximal to the near-infrared camera; and an IV device insertion indicator integrated into the flexible material of the sleeve to indicate the insertion of the catheter into the blood vessel.

* * * * *